United States Patent [19]

Adhikary

[11] 4,204,067
[45] May 20, 1980

[54] DERIVATIVES OF IMIDAZO[2,1-b] THIAZOLE

[76] Inventor: Parimal K. Adhikary, 510 Basswood Dr., Apt. No. 6, Nashville, Tenn. 37209

[21] Appl. No.: 968,090

[22] Filed: Dec. 11, 1978

Related U.S. Application Data

[60] Division of Ser. No. 857,854, Dec. 5, 1977, Pat. No. 4,160,840, which is a continuation of Ser. No. 726,390, Sep. 24, 1976, abandoned.

[51] Int. Cl.² .......................................... C07D 277/08
[52] U.S. Cl. .................... 548/154; 424/270; 548/155
[58] Field of Search ................ 260/306.7 T; 548/154, 548/155

[56] References Cited

U.S. PATENT DOCUMENTS

| 4,014,892 | 3/1977 | Spicer et al. | 260/306.7 T |
| 4,059,588 | 11/1977 | Baklien et al. | 260/306.7 T |
| 4,110,460 | 8/1978 | Baetz | 260/306.7 T |

OTHER PUBLICATIONS

Almirante et al., Jour. Med. Chem. 8, 305 (1965).
Almirante et al., Jour. Me. Chem. 9, 29 (1966).

*Primary Examiner*—Nicholas S. Rizzo
*Attorney, Agent, or Firm*—Sidney B. Willams, Jr.

[57] ABSTRACT

Compounds of the formula:

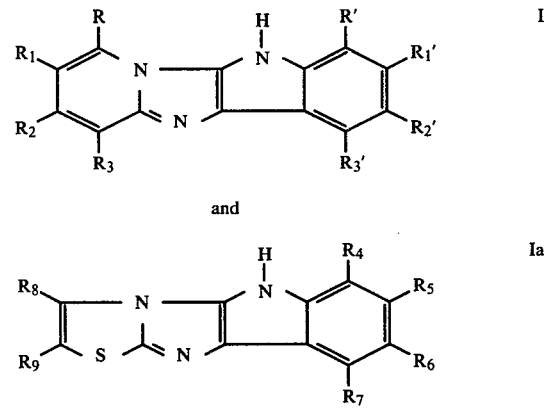

and pharmaceutically acceptable acid addition salts thereof wherein R, $R_1$, $R_2$, $R_3$, are selected from the group consisting of hydrogen, halogen and lower-alkyl of from one to four carbon atoms, inclusive; with the proviso that taken together they constitute the following substituents on the tetracydic ring, 10-halo, 8,10-dihalo, 8,9-di-lower-alkyl, and 7,9-dilower-alkyl; R', $R'_1$, $R'_2$, and $R'_3$ are selected from the group consisting of hydrogen, halogen and lower alkyl of from one to four carbon atoms, inclusive, with the proviso that when taken together they constitute the following substituents, 1-halo, 2-halo, 3-halo, 4-halo, 1-lower-alkyl, 2-lower-alkyl, 3-lower-alkyl, 4-lower-alkyl, 1,3-dihalo, 2,3-dihalo, 2,4-dihalo, 3,4-dihalo, 1,3-di-lower-alkyl, 2,3-di-lower-alkyl, 1,4-di-lower-alkyl; $R_4$, $R_5$, $R_6$, and $R_7$ are selected from the group consisting of hydrogen, halogen and lower-alkyl of from one to four carbon atoms, inclusive, with the proviso that when taken together they constitute the following substituents on the tetracyclic ring, 9-halo, 8-halo, 7-halo, 6-halo, 9-lower-alkyl, 8-lower-alkyl, 7-lower-alkyl, 6-lower-alkyl, 7,9-dihalo, 7,8-dihalo, 6,8,-dihalo, 6,7-dihalo, 79-di-lower-alkyl, 7,9-di-lower-alkyl, 7,8-di-lower-alkyl, and 4,6-di-lower-alkyl. $R_8$ is selected from the group consisting of hydrogen, lower-alkyl of from one to four carbon atoms, inclusive, and $R_9$ is selected from the group consisting of hydrogen and halo. These compounds are useful as anti-hypertensive agents in mammals.

2 Claims, No Drawings

DERIVATIVES OF IMIDAZO[2,1-b] THIAZOLE

This is a division of application Ser. No. 857,854, filed Dec. 5, 1977, now U.S. Pat. No. 4,160,840, which is a continuation of application Ser. No. 726,390, filed Sept. 24, 1976, now abandoned.

BACKGROUND OF THE INVENTION

1. Field of the Invention

The invention concerns novel imidazoindole derivatives and pharmaceutically acceptable acid addition salts thereof; compositions prepared therefrom and methods of their use.

2. Description of the Prior Art

The compound 1,2,3,5-tetrahydroimidazo[2,1-b]quinazoline and some of its derivatives with three-ring systems have structural similarity to our compounds with four ring systems and have been reported by Loev, et al., Journal of Medicinal Chemistry, 15, 727 (1972) and Jen et al., Journal of Medicinal Chemistry. 15, 727 (1972) as effective antihypertensive agent in animals. However, insofar as is presently known, no one has prepared applicants imidazoindole derivatives.

SUMMARY OF THE INVENTION

This invention pertains to some new organic compounds, a process for preparing them, pharmaceutical compositions containing them, and methods of using them. The invention is more particularly directed to derivatives of imidazoindole, and pharmaceutically acceptable acid addition salts thereof having the formula

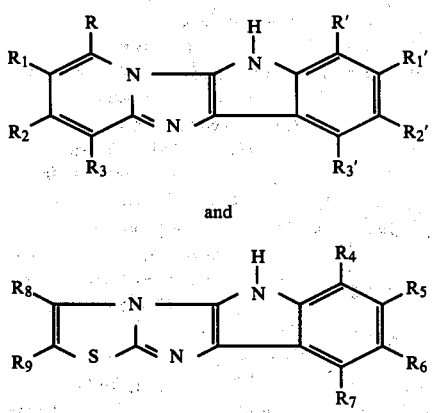

and pharmaceutically acceptable acid addition salts therof wherein R, $R_1$, $R_2$, $R_3$, are selected from the group consisting of hydrogen, halogen and lower-alkyl of from one to four carbon atoms, inclusive; with the proviso that taken together they constitute the following substituents on the tetracyclic ring, 10-halo, 8,10-dihalo, 8,9-di-lower-alkyl, and 7,9-dilower-alkyl; R', $R'_1$, $R'_2$, and $R'_3$ are selected from the group consisting of hydrogen, halogen and lower alkyl of from one to four carbon atoms, inclusive, with the proviso that when taken together they constitute the following substituents on the tetracyclic ring, 1-halo, 2-halo, 3-halo, 4-halo, 1-lower-alkyl, 2-lower-alkyl, 3-lower-alkyl, 4-lower-alkyl, 1,3-dihalo, 2,3-dihalo, 2,4-dihalo, 3,4-dihalo, 1,3-di-lower-alkyl, 2,3-di-lower-alkyl, 1,4-di-lower-alkyl; $R_4$, $R_5$, $R_6$, and $R_7$ are selected from the group consisting of hydrogen, halogen and lower-alkyl of from one to four carbon atoms, inclusive, with the proviso that when taken together they constitute the following substituents on the tetracyclic ring, 9-halo, 8-halo, 7-halo, 6-halo, 9-lower-alkyl, 8-lower-alkyl, 7-lower-alkyl, 6-lower-alkyl, 7,9-dihalo, 7,8-dihalo, 6,8-dihalo, 6,7-dihalo, 7,9-di-lower-alkyl, 7,8-di-lower-alkyl, and 4,6-di-lower-alkyl. $R_8$ is selected from the group consisting of hydrogen, lower-alkyl of from one to four carbon atoms, inclusive, and $R_9$ is selected from the group consisting of hydrogen and halo.

The invention also comprises pharmaceutical dosage unit forms adapted for systemic administration to obtain anti-hypertensive effects in mammals comprising an effective amount of a compound according to formulas I and Ia, or a pharmaceutically acceptable acid addition salt thereof, in combination with pharmaceutical means which adapt such compounds for systemic administration.

Further the invention relates to methods of treating hypertension in mammals, for example humans and valuable warm-blooded animals such as laboratory rats, dogs, cats and other domestic animals by administering systemically to the mammals, the aforesaid pharmaceutical dosage unit forms supplying an effective amount for hypertensive.

DETAILED DESCRIPTION OF THE INVENTION

Most of the compounds of formulae I and Ia are prepared by the phosphite reduction of the corresponding nitroso compounds. The reduction of a nitroso compound by triethylphosphite is described by J. I. Cadogan, Synthesis, 1, II (1972). The nitroso intermediates of pyridine and thiazole are prepared by condensation of an α-haloacetophenone respectively with 2-aminopyridine and 2-aminothiazole as described by Almirante et al., Journal of Medicinal Chemistry, 8, 305 (1968) and Almirante et al., Journal of Medicinal Chemistry 9, 29 (1966) and then nitrosation of the resulting base with sodium nitrite and acetic acid as described by La Rocca et al., Journal of Pharmaceutical Sciences, 60, 74 (1971).

The preferred method of recovering the imidazoindoles from the phosphite reduction mixture is to let the mixture solidify (about 24 hours required), wash with carbon tetrachloride on a glass filter and recrystallize the residue two times from 2-propanol.

The imidazoindoles may also be recovered from the phosphite reduction mixture by allowing it to solidify, washing the solid on a glass filter with cold carbon tetrachloride, taking the residue in a small quantity of chloroform, and eluating it over a column of activated alumina (80–325 mash). The first colored zone is collected, evaporated to dryness and then recrystallized once from 2-propanol.

For the synthesis of most of imidazo-indole derivatives of my invention, known phenacyl halides or their ring substituted derivatives are used for condensation respectively with 2-Aminopyridines or 2-Aminothiazoles. In those isolated cases where a phenacyl halide with a desired halogen substitution in the ring is not readily available, the desired substitution in the phenyl ring is accomplished by first synthesizing the respective tetracyclic compound without the phenyl ring substituent and later introducing the desired substituent by halogenation. For example: meta-halo-phenacyl halides are not readily available. Therefore the synthesis of 4-halo-5H-pyrido [2', 1':2, 3] imidazo [4, 5-b] indoles or 6-halo-5H-thiazolo [2', 3':2, 3] imidazo [4, 5-b] indoles are achieved by subsequent halogenation of the respective unsubstituted tetracyclic imidazo-indole derivatives.

The condensation reaction and subsequent phosphite reductions may be represented schematically as follows:

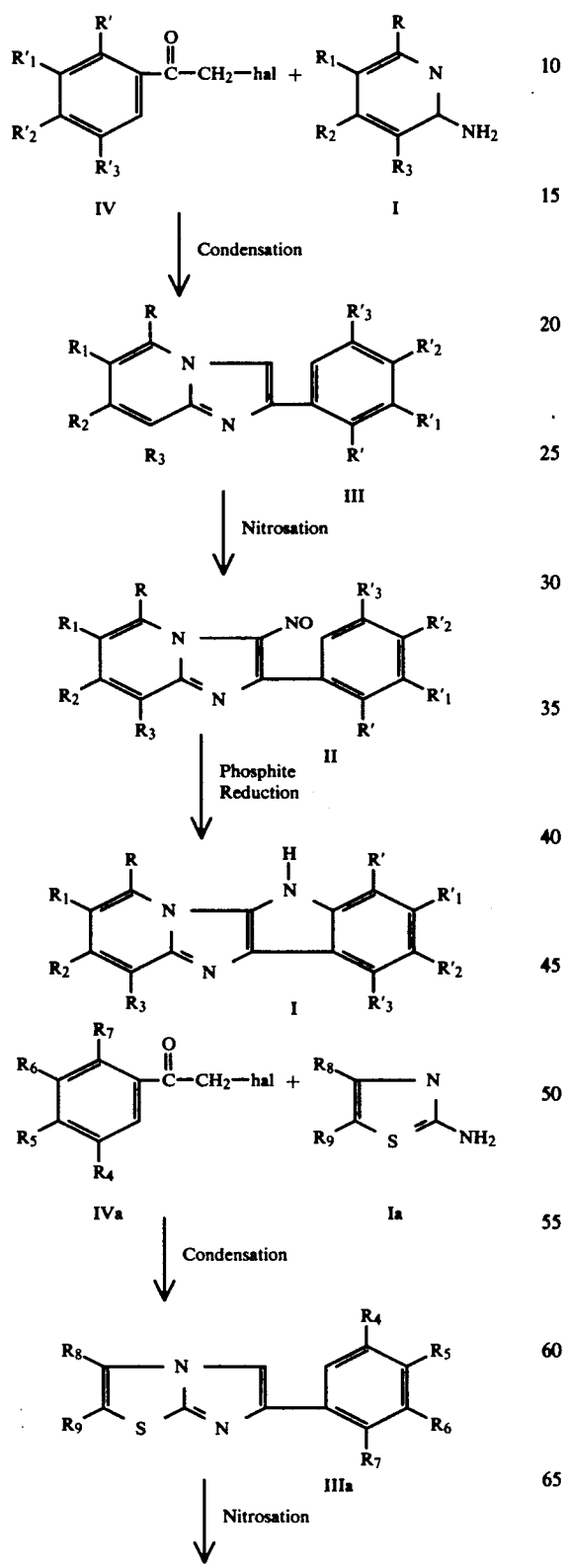

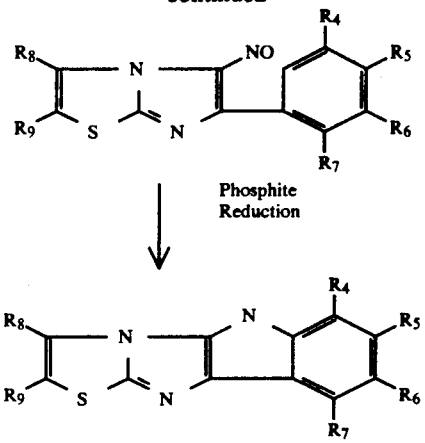

wherein R, $R_1$, $R_2$, $R_3$, are selected from the group consisting of hydrogen, halogen and lower-alkyl of from one to four carbon atoms, inclusive; with the proviso that taken together they constitute the following substituents on the tetracyclic ring, 10-halo, 8,10-dihalo, 8,9-di-lower-alkyl, and 7,9-dilower-alkyl; R', $R'_1$, $R'_2$, and $R'_3$ are selected from the group consisting of hydrogen, halogen and lower alkyl of from one to four carbon atoms, inclusive, with the proviso that when taken together they constitute the following substituents on the tetracyclic ring, 1-halo, 2-halo, 3-halo, 1-lower-alkyl, 2-lower-alkyl, 3-lower-alkyl, 4-lower alkyl, 1,3-dihalo, 2,3-dihalo, 2,4-dihalo, 3,4-dihalo, 1,3-di-lower-alkyl, 2,3-di-lower-alkyl, 1,4-di-lower-alkyl; $R_4$, $R_5$, $R_6$, and $R_7$ are selected from the group consisting of hydrogen, halogen and lower-alkyl of from one to four carbon atoms, inclusive, with the proviso that when taken together they constitute the following substituents on the tetracyclic ring, 9-halo, 8-halo, 7-halo, 9-lower-alkyl, 8-lower-alkyl, 7-lower-alkyl, 6-lower-alkyl, 7,9-dihalo, 7,8-dihalo, 6,8-dihalo, 6,7-dihalo, 7,9-di-lower-alkyl, 7,9-di-lower-alkyl, 7,8-di-lower-alkyl, and 4,6-di-lower-alkyl. $R_8$ is selected from the group consisting of hydrogen, lower-alkyl of from one to four carbon atoms, inclusive, and $R_9$ is selected from the group consisting of hydrogen and halo.

In the foregoing designation of variables, lower-alkyl means methyl, ethyl, propyl, isopropyl, butyl and the isomeric forms thereof. Halo means chloro, bromo, iodio and fluoro.

When a pyridine derivative, the phosphite reduction is complete with 15–30 minute of refluxing. Further heating yields gradual decomposition of this derivative. The thiazole derivative, formula Ia does not degrade upon prolonged heating during the reduction step.

Pharmaceutically acceptable acid addition salts of the compounds (I) are prepared by reacting a compound of formula (I) free base with a stoichoimetric amount of an acid, such as hydrogen chloride, hydrogen bromide, hydrogen iodide, sulfuric acid, phosphoric acid, acetic acid, lactic acid, citric acid, succinic acid, benzoic acid, salicylic acid, pamoic acid, cyclohexanesulfamic acid, and the like.

This invention relates also to pharmaceutical dosage unit forms for systemic administration (oral and parenteral administration) for treating hypertensive mammals, including humans. The term "dosage unit form"

as used in this specification and in the claims refers to physically discrete units suitable as unitary dosages for mammalian subjects, each unit containing a pre-determined quantity of the essential active ingredient, i.e., a compound (I) or a pharmaceutically acceptable acid addition salt thereof calculated to produce the desired effect in combination with the required pharmaceutical means which adapt the said ingredient for systemic administration. Examples of dosage unit forms in accordance with this invention are tablets, capsules, orally administered liquid preparations in liquid vehicles, sterile preparations in liquid vehicles for intramuscular and intravenous administration, suppositories, and sterile dry preparations for the extemporaneous preparation of sterile injectable preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate and the like. Liquid preparations for oral administration are prepared in water or aqueous vehicles which advantageously contain suspending agents, such as for example, ethanol, sodium carboxymethylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example sugars or sodium chloride. Carriers and vehicles include vegetable oils, ethanol and polyols, for example, glycerol, propylene glycol, liquid polyethylene glycol, and the like. Any solid preparations for subsequent extemporaneous preparation of sterile injectable preparations are sterilized, preferably by exposure to a sterilizing gas, such as for example ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 10 mg. to about 100 mg. of the essential active ingredient per dosage unit form. The amount of the essential active ingredient provided in the pharmaceutical dosage unit forms is based on my finding that the effective amount of compounds of the invention and acid addition salts thereof, for obtaining a hypotensive effect in mammals is within a range from about 10 mg. per kg. to about 100 mg. per/kg. of body weight of the recipient, daily.

The following examples and preparations describe the manner and process of making and using the invention and set forth the best mode contemplated by the inventor of carrying out the invention but are not to be construed as limiting.

Preparation 1: 3-nitroso-2-phenylimidazo[1,2-a]pyridine (A) A mixture of 9.5 g. of 2-aminopyridine (0.1 mole) 20 g. of α-bromoacetophenone (0.1 mol.) and 200 ml. of 95% ethanol is refluxed for three hours and then heated at 60° C. for an additional 12 hours. After cooling, the reaction product is condensed to a thick liquid by evaporating it in a rotary evaporator. The residue is mixed with 500 ml. of chloroform and 100 ml. of 3 N sodium hydroxide. The mixture is stirred for 10 minutes at room temperature and then separated in a separatory funnel. The lower layer is collected, washed with 100 ml. of water and then evaporated. The residue is washed with two propanol on a glass filter and dried in a vacuum to yield 20 g. of 2-phenylimidazo[1,2-a]pyridine.

(B) A mixture of 20 g. of 2-phenylimidazo[1,2-a]pyridine and 200 ml. of glacial acetic acid is stirred at room temperature until the 2-phenylimidazo[1,2-a]pyridine is completely dissolved. The acetic acid solution is diluted with 20 ml. of water and cooled to 0° to 5° C. in an ice-salt bath. A solution of 15 g. of $NaNO_2$ in 50 ml. of water is added dropwise to the cooled acetic acid solution while the solution is constantly stirred by a mechanical stirrer. The temperature of the solution is kept below 5° C. during the addition of the $NaNO_2$ solution and three hours thereafter. Three hours after the completion of $NaNO_2$ additon, the reaction mixture is further stirred at room temperature for 12 more hours. The green precipitate is filtered and washed thoroughly with $H_2O$ on a glass filter. The residue is recrystallized once from ethanol to yield 15 g., 3-nitroso-2-phenylimidazo[1,2-a]pyridine, m.p. 165°–167°.

Preparation 2: 5-nitroso-6-phenylimidazo[2,1-b]thiazole (A) A mixture of 11 g. of 2-aminothiazole (97%, 0.1 mole) 20 g. of α-bromoacetophenone (0.1 mol) and 200 ml. of 95% ethanol is refluxed for three hours and then heated at 60° C. for an additional 12 hours. After cooling, the reaction product is condensed to a thick liquid by evaporating it in a rotary evaporator. The residue is mixed with 500 ml. of chloroform and 100 ml. of 3 N sodium hydroxide. The mixture is stirred for 10 minutes at room temperature and then separated in a separatory funnel. The lower layer is collected, washed with 100 ml. of water and then evaporated. The residue is washed with two propanol on a glass filter and dried in a vacuum to yield 20 g. of 6-phenylimidazo[2,1-b]thiazole.

(B) A mixture of 20 g. of 6-phenylimidazo[2,1-b]thiazole and 200 ml. of glacial acetic acid is stirred at room temperature until the 2-phenylimidazo[1,2-a]pyridine is completely dissolved. The acetic acid solution is diluted with 20 ml. of water and cooled to 0° to 5° C. in an ice-salt bath. A solution of 15 g. of $NaNO_2$ in 50 ml. of water is added dropwise to the cooled acetic acid solution while the solution is constantly stirred by a mechanical stirrer. The temperature of the solution is kept below 5° C. during the addition of the $NaNO_2$ solution and three hours thereafter. Three hours after the completion of $NaNO_2$ addition, the reaction mixture is further stirred at room temperature for 12 more hours. The blueish green precipitate is filtered and washed thoroughly with $H_2O$ on a glass filter. The residue is recrystallized once from acetone to yield 12 g. of 5-nitroso-6-phenylimidazo[2,1-b]thiazole, m.p. 175°–177° C.

EXAMPLE 1

Preparation of 5H-pyrido[2',1':2,3]imidiazo[4,5-b]indole

A mixture of 9.0 grams of analytically pure 3-nitroso-2-phenylimidazo[1,2-a]pyridine (0.04 mol) and 10 ml. of 97% triethyl phosphite (0.05 mol) in 50 ml. of anhydrous toluene is refluxed for 15–30 minutes with stirring and under a constant flow of dry nitrogen gas. The temperature of the oil bath is kept between 110° and 120° C. After cooling, the solvent and excess triethyl phosphite are removed by vacuum distillation at 0.2 Torr. The temperature of the oil bath is kept under 120° C., also during the distillation. The residue which is a thick oily liquid is kept overnight at 0° C. during which time it solidified. The solid is washed on a glass filter with cold carbon tetrachloride and then recrystallized twice from 2-propanol to yield 4 g. of 5H-pyrido[2',1':2,3]imidazo[4,5-b]indole, m.p. 78°–80° C.

Analysis Calc'd for: $C_{13}H_9N_3$: C, 75.33; H, 4.34; N, 20.22. Found: C, 75.17; H, 4.38; N, 20.29.

EXAMPLE 2

Preparation of
1-methyl-5H-pyrido[2',1':2,3]imidazo[4,5-b]indole

Utilizing the procedure of Example 1 and substituting 3-nitroso-2-(1-methylphenyl)imidazo[1,2-a]pyridine for 3-nitroso-2-phenylimidazo[1,2-a]pyridine there is obtained 1-methyl-5H-pyrido[2',1':2,3]imidazo[4,5-b]indole.

EXAMPLE 3

Preparation of
3-chloro-5H-pyrido[2',1':2,3]imidazo[4,5-b]indole

Utilizing the procedure of Example 1 and substituting 3-nitroso-2-(3-chlorophenyl)imidazo[1,2-a]pyridine for 3-nitroso-2-phenylimidazo[1,2-a]pyridine there is obtained 3-chloro-5H-pyrido[2',1':2,3]imidazo[4,5-b]indole.

EXAMPLE 4

Preparation of
10-methyl-5H-pyrido[2',1':2,3]imidazo[4,5-b]indole

Utilizing the procedure of Example 1 and substituting 10-methyl-3-nitroso-2-phenylimidazo[1,2-a]pyridine for 3-nitroso-2-phenylimidazo[1,2-a]pyridine there is obtained 10-methyl-5H-pyrido[2',1':2,3]imidazo[4,5-b]indole.

EXAMPLE 5

Preparation of
8-chloro-5H-pyrido[2',1':2,3]imidazo[4,5-b]indole

Utilizing the procedure of Example 1 and substituting 8-chloro-3-nitroso-2-phenylimidazo[1,2-a]pyridine for 3-nitroso-2-phenylimidazo[1,2-a]pyridine there is obtained 8-chloro-5H-pyrido[2',1':2,3]imidazo[4,5-b]indole.

Utilizing the procedures of Example 1, and substituting the appropriate nitroso compounds, the following derivatives of pyridoimidazolindole are prepared.

1-methyl-5H-pyrido[2',1':2,3]imidazo[4,5-b]indole,
2-methyl-5H-pyrido[2',1':2,3]imidazo[4,5-b]indole,
3-methyl-5H-pyrido[2',1':2,3]imidazo[4,5-b]indole,
4-methyl-5H-pyrido[2,',1':2,3]imidazo[4,5-b]indole,
7-methyl-5H-pyrido[2',1':2,3]imidazo[4,5-b]indole,
8-methyl-5H-pyrido[2',1':2,3]imidazo[4,5-b]indole,
9-methyl-5H-pyrido[2',1':2,3]imidazo[4,5-b]indole,
10-methyl-5H-pyrido[2',1':2,3]imidazo[4,5-b]indole,
1-ethyl-5H-pyrido[2',1':2,3]imidazo[4,5-b]indole,
2-ethyl-5H-pyrido[2',1':2,3]imidazo[4,5-b]indole,
3-ethyl-5H-pyrido[2',1':2,3]imidazo[4,5-b]indole,
4-ethyl-5H-pyrido[2',1':2,3]imidazo[4,5-b]indole,
7-ethyl-5H-pyrido[2',1':2,3]imidazo[4,5-b]indole,
8-ethyl-5H-pyrido[2',1':2,3]imidazo[4,5-b]indole,
9-ethyl-5H-pyrido[2',1':2,3]imidazo[4,5-b]indole,
10-ethyl-5H-pyrido[2',1':2,3]imidazo[4,5-b]indole,
1-propyl-5H-pyrido[2',1':2,3]imidazo[4,5-b]indole,
2-propyl-5H-pyrido[2',1':2,3]imidazo[4,5-b]indole,
3-propyl-5H-pyrido[2',1':2,3]imidazo[4,5-b]indole,
4-propyl-5H-pyrido[2',1':2,3]imidazo[4,5-b]indole,
7-propyl-5H-pyrido[2',1':2,3]imidazo[4,5-b]indole,
8-propyl-5H-pyrido[2',1':2,3]imidazo[4,5-b]indole,
9-propyl-5H-pyrido[2',1':2,3]imidazo[4,5-b]indole,
10-propyl-5H-pyrido[2',1':2,3]imidazo[4,5-b]indole,
1-isopropyl-5H-pyrido[2',1':2,3]imidazo[4,5-b]indole,
2-isopropyl-5H-pyrido[2',1':2,3]imidazo[4,5-b]indole,
3-isopropyl-5H-pyrido[2',1':2,3]imidazo[4,5-b]indole,
4-isopropyl-5H-pyrido[2',1':2,3]imidazo[4,5-b]indole,
7-isopropyl-5H-pyrido[2',1':2,3]imidazo[4,5-b]indole,
8-isopropyl-5H-pyrido[2',1':2,3]imidazo[4,5-b]indole,
9-isopropyl-5H-pyrido[2',1':2,3]imidazo[4,5-b]indole,
10-isopropyl-5H-pyrido[2',1':2,3]imidazo[4,5-b]indole,
1-n-butyl-5H-pyrido[2',1':2,3]imidazo[4,5-b]indole,
2-n-butyl-5H-pyrido[2',1':2,3]imidazo[4,5-b]indole,
3-n-butyl-5H-pyrido[2',1':2,3]imidazo[4,5-b]indole,
4-n-butyl-5H-pyrido[2',1':2,3]imidazo[4,5-b]indole,
7-n-butyl-5H-pyrido[2',1':2,3]imidazo[4,5-b]indole,
8-n-butyl-5H-pyrido[2',1':2,3]imidazo[4,5-b]indole,
9-n-butyl-5H-pyrido[2',1':2,3]imidazo[4,5-b]indole,
10-n-butyl-5H-pyrido[2',1':2,3]imidazo[4,5-b]indole,
1-sec-butyl-5H-pyrido[2',1':2,3]imidazo[4,5-b]indole,
2-sec-butyl-5H-pyrido[2',1':2,3]imidazo[4,5-b]indole,
3-sec-butyl-5H-pyrido[2',1':2,3]imidazo[4,5-b]indole,
4-sec-butyl-5H-pyrido[2',1':2,3]imidazo[4,5-b]indole,
7-sec-butyl-5H-pyrido[2',1':2,3]imidazo[4,5-b]indole,
8-sec-butyl-5H-pyrido[2',1':2,3]imidazo[4,5-b]indole,
9-sec-butyl-5H-pyrido[2',1':2,3]imidazo[4,5-b]indole,
10-sec-butyl-5H-pyrido[2',1':2,3]imidazo[4,5-b]indole,
1-t-butyl-5H-pyrido[2',1':2,3]imidazo[4,5-b]indole,
2-t-butyl-5H-pyrido[2',1':2,3]imidazo[4,5-b]indole,
3-t-butyl-5H-pyrido[2',1':2,3]imidazo[4,5-b]indole,
4-t-butyl-5H-pyrido[2',1':2,3]imidazo[4,5-b]indole,
7-t-butyl-5H-pyrido[2',1':2,3]imidazo[4,5-b]indole,
8-t-butyl-5H-pyrido[2',1':2,3]imidazo[4,5-b]indole,
9-t-butyl-5H-pyrido[2',1':2,3]imidazo[4,5-b]indole,
10-t-butyl-5H-pyrido[2',1':2,3]imidazo[4,5-b]indole,
1-chloro-5H-pyrido[2',1':2,3]imidazo[4,5-b]indole,
2-chloro-5H-pyrido[2',1':2,3]imidazo[4,5-b]indole,
3-chloro-5H-pyrido[2',1':2,3]imidazo[4,5-b]indole,
7-chloro-5H-pyrido[2',1':2,3]imidazo[4,5-b]indole,
8-chloro-5H-pyrido[2',1':2,3]imidazo[4,5-b]indole,
9-chloro-5H-pyrido[2',1':2,3]imidazo[4,5-b]indole,
10-chloro-5H-pyrido[2',1':2,3]imidazo[4,5-b]indole,
1-bromo-5H-pyrido[2',1':2,3]imidazo[4,5-b]indole,
2-bromo-5H-pyrido[2',1':2,3]imidazo[4,5-b]indole,
3-bromo-5H-pyrido[2',1':2,3]imidazo[4,5-b]indole,
7-bromo-5H-pyrido[2',1':2,3]imidazo[4,5-b]indole,
8-bromo-5H-pyrido[2',1':2,3]imidazo[4,5-b]indole,
9-bromo-5H-pyrido[2',1':2,3]imidazo[4,5-b]indole,
10-bromo-5H-pyrido2',1':2,3]imidazo[4,5-b]indole,
1-fluoro-5H-pyrido[2',1':2,3]imidazo[4,5-b]indole,
2-fluoro-5H-pyrido[2',1':2,3]imidazo[4,5-b]indole,
3-fluoro-5H-pyrido[2',1':2,3]imidazo[4,5-b]indole,
7-fluoro-5H-pyrido[2',1':2,3]imidazo[4,5-b]indole,
8-fluoro-5H-pyrido[2',1':2,3]imidazo[4,5-b]indole,
9-fluoro-5H-pyrido[2',1':2,3]imidazo[4,5-b]indole,
10-fluoro-5H-pyrido[2',1':2,3]imidazo[4,5-b]indole,
1-iodo-5H-pyrido[2',1':2,3]imidazo[4,5-b]indole,
2-iodo-5H-pyrido[2',1':2,3]imidazo[4,5-b]indole,
3-iodo-5H-pyrido[2',1':2,3]imidazo[4,5-b]indole, 7-iodo-5H-pyrido[2′,1′:2,3]imidazo[4,5-b]indole,
8-iodo-5H-pyrido[2′,1′:2,3]imidazo[4,5-b]indole,
9-iodo-5H-pyrido[2′,1′:2,3]imidazo[4,5-b]indole,
10-iodo-5H-pyrido[2′,1′:2,3]imidazo[4,5-b]indole,
1,3-dichloro-5H-pyrido[2′,1′:2,3]imidazo[4,5-b]indole,
2,3-dichloro-5H-pyrido[2′,1′:2,3]imidazo[4,5-b]indole,
2,4-dichloro-5H-pyrido[2′,1′:2,3]imidazo[4,5-b]indole,
3,4-chloro-5H-pyrido[2′,1′:2,3]imidazo[4,5-b]indole,
1,3-dibromo-5H-pyrido[2′,1′:2,3]imidazo[4,5-b]indole,
2,3-dibromo-5H-pyrido[2′,1′:2,3]imidazo[4,5-b]indole,
2,4-dibromo-5H-pyrido[2′,1′:2,3]imidazo[4,5-b]indole,
3,4-dibromo-5H-pyrido[2′,1′:2,3]imidazo[4,5-b]indole,
8,10-dichloro-5H-pyrido[2′,1′:2,3]imidazo[4,5-b]indole,
8,10-dibromo-5H-pyrido[2′,1′:2,3]imidazo[4,5-b]indole,
7,9-dimethyl-5H-pyrido[2′,1′:2,3]imidazo[4,5-b]indole,
7,9-diethyl-5H-pyrido[2′,1′:2,3]imidazo[4,5-b]indole,
7,9-dipropyl-5H-pyrido[2′,1′:2,3]imidazo[4,5-b]indole,
7,9-diisopropyl-5H-pyrido[2′,1′:2,3]imidazo[4,5-b]indole,
7,9-di-n-butyl-5H-pyrido[2′,1′:2,3]imidazo[4,5-b]indole,
8,9-dimethyl-5H-pyrido[2′,1′:2,3]imidazo[4,5-b]indole,
8,9-diethyl-5H-pyrido[2′,1′:2,3]imidazo[4,5-b]indole,
8,9-dipropyl-5H-pyrido[2′,1′:2,3]imidazo[4,5-b]indole,
8,9-diisopropyl-5H-pyrido[2′,1′:2,3]imidazo[4,5-b]indole,
1,7-dimethyl-5H-pyrido[2′,1′:2,3]imidazo[4,5-b]indole,
1,8-dimethyl-5H-pyrido[2′,1′:2,3]imidazo[4,5-b]indole,
1,9-dimethyl-5H-pyrido[2′,1′:2,3]imidazo[4,5-b]indole,
1,10-dimethyl-5H-pyrido[2′,1′:2,3]imidazo[4,5-b]indole,
2,7-dimethyl-5H-pyrido[2′,1′:2,3]imidazo[4,5-b]indole,
2,8-dimethyl-5H-pyrido[2′,1′:2,3]imidazo[4,5-b]indole,
2,9-dimethyl-5H-pyrido[2′,1′:2,3]imidazo[4,5-b]indole,
2,10-dimethyl-5H-pyrido[2′,1′:2,3]imidazo[4,5-b]indole,
3,7-dimethyl-5H-pyrido[2′,1′:2,3]imidazo[4,5-b]indole,
3,8-dimethyl-5H-pyrido[2′,1′:2,3]imidazo[4,5-b]indole,
3,9-dimethyl-5H-pyrido[2′,1′:2,3]imidazo[4,5-b]indole,
3,10-dimethyl-5H-pyrido[2′,1′:2,3]imidazo[4,5-b]indole,
4,7-dimethyl-5H-pyrido[2′,1′:2,3]imidazo[4,5-b]indole,
4,8-dimethyl-5H-pyrido[2′,1′:2,3]imidazo[4,5-b]indole,
4,9-dimethyl-5H-pyrido[2′,1′:2,3]imidazo[4,5-b]indole,
4,10-dimethyl-5H-pyrido[2′,1′:2,3]imidazo[4,5-b]indole,
2,4-dimethyl-5H-pyrido[2′,1′:2,3]imidazo[4,5-b]indole,
10-chloro-4-methyl-5H-pyrido[2′,1′:2,3]imidazo[4,5-b]indole,
10-bromo-4-methyl-5H-pyrido[2′,1′:2,3]imidazo[4,5-b]indole,
10-chloro-4-ethyl-5H-pyrido[2′,1′:2,3]imidazo[4,5-b]indole,
10-chloro-4-butyl-5H-pyrido[2′,1′:2,3]imidazo[4,5-b]indole,
10-chloro-4-propyl-5H-pyrido[2′,1′:2,3]imidazo[4,5-b]indole,
10-chloro-2,4-dimethyl-5H-pyrido[2′,1′:2,3]imidazo[4,5-b]indole,
10-chloro-2,4-diethyl-5H-pyrido[2′,1′:2,3]imidazo[4,5-b]indole,
10-chloro-2,4-dipropyl-5H-pyrido[2′,1′:2,3]imidazo[4,5-b]indole,
10-chloro-2,4-dibutyl-5H-pyrido[2′,1′:2,3]imidazo[4,5-b]indole,
4,10-dichloro-5H-pyrido[2′,1′:2,3]imidazo[4,5-b]indole,
4,10-dibromo-5H-pyrido[2′,1′:2,3]imidazo[4,5-b]indole,
10-chloro-2,4-dichloro-5H-pyrido[2′,1′:2,3]imidazo[4,5-b]indole,
10-bromo-2,4-dibromo-5H-pyrido[2′,1′:2,3]imidazo[4,5-b]indole,
10-chloro-2,4-dibromo-5H-pyrido[2′,1′:2,3]imidazo[4,5-b]indole,
10-bromo-2,4-dichloro-5H-pyrido[2′,1′:2,3]imidazo[4,5-b]indole,
4-chloro-9-methyl-5H-pyrido[2′,1′:2,3]imidazo[4,5-b]indole,
2,4-dichloro-9-methyl-5H-pyrido[2′,1′:2,3]imidazo[4,5-b]indole,
2,4-dichloro-9-ethyl-5H-pyrido[2′,1′:2,3]imidazo[4,5-b]indole,
2,4-dichloro-9-propyl-5H-pyrido[2′,1′:2,3]imidazo[4,5-b]indole,
2,4-dichloro-9-butyl-5H-pyrido[2′,1′:2,3]imidazo[4,5-b]indole,
2,4-dibromo-9-methyl-5H-pyrido[2′,1′:2,3]imidazo[4,5-b]indole,
2,4-dibromo-9-ethyl-5H-pyrido[2′,1′:2,3]imidazo[4,5-b]indole,
2,4-dibromo-9-propyl-5H-pyrido[2′,1′:2,3]imidazo[4,5-b]indole,
2,4-dibromo-9-butyl-5H-pyrido[2′,1′:2,3]imidazo[4,5-b]indole,

EXAMPLE 6

Preparation of 5H-thiazolo[2′,3′:2,3]imidazo[4,5-b]indole

A mixture of 8.5 grams of analytically pure 5-nitroso-6-phenylimidazo[2,1-b]thiazole (0.04 mole) and 10 ml. of triethylphosphite (0.05 mole) in 50 ml. of anhydrous toluene is refluxed for three hours with constant stirring and under a constant flow of dry nitrogen. The temperature of the oil bath is kept between 110° and 120° C. After cooling, the toluene and excess triethyl phosphite are removed by vacuum distillation at 0.2 Torr. The temperature of the oil bath is kept under 120° C. also during the distillation. The residue which is a thick oily liquid is kept over night at 0° C., during which time it solidifies. The solid is washed on a glass filter with cold carbon tetrachloride and then recrystallized twice from 2-propanol to yield three grams of 5H-thiazolo[2′,3′:2,3]imidazo[4,5-b]indole.

Analysis Calc'd for: $C_{11}H_7N_3S$: C, 61.95; H, 3.30; N, 19.70; S, 15.00. Found: C, 61.90; H, 3.34; N, 19.61; S, 15.07.

EXAMPLE 7

Preparation of 7-methyl-5H-thiazolo[2′,3′:2,3]imidazo[4,5-b]indole

Utilizing the procedure of Example 6 and substituting 5-nitroso-6-(4-methylphenyl)imidazo[2,1-b]thiazole for 5-nitroso-6-phenylimidazo[2,1-b]thiazole there is obtained 7-methyl-5H-thiazolo[2′,3′:2,3]imidazo[4,5-b]indole.

EXAMPLE 8

Preparation of 7-chloro-5H-thiazolo[2′,3′:2,3]imidazo[4,5-b]indole

Utilizing the procedure of Example 6 and substituting 5-nitroso-6-(4-chlorophenyl)imidazo[2,1-b]thiazole for 5-nitroso-6-phenylimidazo[2,1-b]thiazole there is obtained 7-chloro-5H-thiazolo[2′,3′:2,3]imidazo[4,5-b]indole.

EXAMPLE 9

Preparation of 3-methyl-5H-thiazolo[2′,3′:2,3]imidazo[4,5-b]indole

Utilizing the procedures of Example 6 and substituting 3-methyl-5-nitroso-6-phenylimidazo[2,1-b]thiazole for 5-nitroso-6-phenylimidazo[2,1-b]thiazole there is obtained 3-methyl-5H-thiazole[2',3':2,3]imidazo[4,5-b]indole.

EXAMPLE 10

Preparation of 2-chloro-5H-thiazolo[2',3':2,3]imidazo[4,5-b]indole.

Utilizing the procedures of Example 6 and substituting 2-chloro-5-nitroso-6-phenylimidazo[2,1-b]thiazole for 5-nitroso-6-phenylimidazo[2,1-b]thiazole there is obtained 2-chloro-5H-thiazolo[2',3':2,3]imidazo[4,5-b]indole.

Further utilizing the procedure of Example 6 and substituting the appropriate nitroso compounds, the following derivatives of thiazolo imidazoindoles are prepared
3-bromo-5H-thiazolo[2',3':2,3]imidazolo[4,5-b]indole,
7-bromo-5H-thiazolo[2',3':2,3]imidazolo[4,5-b]indole,
7,9-dimethyl-5H-thiazolo[2',3':2,3]imidazolo[4,5-b]indole,
7,9-dichloro-5H-thiazolo[2',3':2,3]imidazolo[4,5-b]indole,
7,9-dibromo-5H-thiazolo[2',3':2,3]imidazolo[4,5-b]indole, Starting materials for preparing the nitroso-thiazoles and nitroso-pyridines of this invention are available or can be prepared by methods described in the prior art.

I claim:
1. A compound having the formula

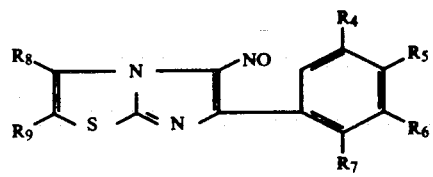

wherein $R_4$, $R_5$, $R_6$, and $R_7$ are selected from the group consisting of hydrogen, halogen and lower-alkyl of from one to four carbon atoms, inclusive, with the proviso that when taken together they constitute the following substituents on the tetracyclic ring, 9-halo, 8-halo, 7-halo, 6-halo, 9-lower-alkyl, 8-lower-alkyl, 7-lower-alkyl, 6-lower-alkyl, 7,9-dihalo, 7,8-dihalo, 6,8-dihalo, 6,7-dihalo, 7,9-di-lower-alkyl, 7,8-di-lower-alkyl and 4,6-di-lower-alkyl; $R_8$ is selected from the group consisting of hydrogen, lower-alkyl of from one to four carbon atoms, inclusive, and $R_9$ is selected from the group consisting of hydrogen and halo.

2. A compound according to claim 1 having the formula 1a and wherein $R_4$, $R_5$, $R_6$, $R_7$, $R_8$ and $R_9$ are all hydrogen, so that the specific compound is 5-nitroso-6-phenylimidazo[2,1-b]thiazole.

* * * * *

UNITED STATES PATENT OFFICE
CERTIFICATE OF CORRECTION

Patent No. 4,204,067      Dated May 20, 1978

Inventor(s) Parimal K. Adhikary

It is certified that error appears in the above-identified patent and that said Letters Patent are hereby corrected as shown below:

Page 1, ABSTRACT: "79-di-lower-alkyl, 7,9-di-lower-alkyl," should read: -- 7,9-di-lower-alkyl, --.

Column 4, lines 43-44: "7,9-di-lower-alkyl, 7,9-di-lower-alkyl," should read: -- 7,9-di-lower alkyl, --.

Column 5, line 67: "α-bromoacetophenone" should read: -- ω-bromo-acetophenone --.

Column 6, line 32: "α-bromoacetophenone" should read: -- ω-bromo-acetophenone --.

Column 9, line 8: "3,4-chloro" should read: -- 3,4-dichloro- --.

Signed and Sealed this

Twenty-third Day of November 1982

[SEAL]

Attest:

GERALD J. MOSSINGHOFF

Attesting Officer     Commissioner of Patents and Trademarks